(12) United States Patent
Kudo

(10) Patent No.: US 11,075,004 B2
(45) Date of Patent: Jul. 27, 2021

(54) DISCRIMINATION RESULT PROVIDING APPARATUS, OPERATING METHOD OF DISCRIMINATION RESULT PROVIDING APPARATUS, DISCRIMINATION RESULT PROVIDING PROGRAM, AND DISCRIMINATION RESULT PROVIDING SYSTEM

(71) Applicant: FUJIFILM Corporation, Tokyo (JP)

(72) Inventor: Yuya Kudo, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 502 days.

(21) Appl. No.: 16/129,950

(22) Filed: Sep. 13, 2018

(65) Prior Publication Data

US 2019/0103185 A1 Apr. 4, 2019

(30) Foreign Application Priority Data

Sep. 29, 2017 (JP) .............................. JP2017-189992

(51) Int. Cl.
| | |
|---|---|
| *G16H 40/20* | (2018.01) |
| *G16H 30/40* | (2018.01) |
| *G06K 9/62* | (2006.01) |
| *G06N 3/04* | (2006.01) |
| *G16H 50/20* | (2018.01) |
| *G16H 50/70* | (2018.01) |
| *G06K 9/46* | (2006.01) |

(52) U.S. Cl.
CPC ............ *G16H 40/20* (2018.01); *G06K 9/4628* (2013.01); *G06K 9/627* (2013.01); *G06K 9/6256* (2013.01); *G06N 3/0454* (2013.01); *G16H 30/40* (2018.01); *G16H 50/20* (2018.01); *G16H 50/70* (2018.01); *G06K 2209/05* (2013.01)

(58) Field of Classification Search
CPC ........ G16H 40/20; G16H 50/70; G16H 50/20; G16H 30/40; G06K 9/4628; G06K 9/6256; G06K 9/627; G06K 2209/05; G06N 3/0454
USPC ....................................................... 705/2-3
See application file for complete search history.

(56) References Cited

U.S. PATENT DOCUMENTS

| | | | |
|---|---|---|---|
| 9,916,538 B2* | 3/2018 | Zadeh ................... | G06K 9/627 |
| 10,915,990 B2* | 2/2021 | Lebel ..................... | G06K 9/40 |

(Continued)

FOREIGN PATENT DOCUMENTS

JP 2011-154532 A 8/2011

*Primary Examiner* — Michael Tomaszewski
(74) *Attorney, Agent, or Firm* — Birch, Stewart, Kolasch & Birch, LLP

(57) ABSTRACT

Image correct data is received from a plurality of terminals that belong to a plurality of organizations, a learning-terminated discriminator that is a learning discriminator that has performed learning using the image correct solution data is obtained, distribution of resources capable of being used by each discriminator is determined in accordance with the number of pieces of the received image correct solution data or the degree of performance improvement of the learning-terminated discriminator, and a discrimination result "Output" obtained by performing discrimination of a discrimination target image "Input" received from the terminal using the determined resources of the distribution is transmitted to the terminal that is a transmission source.

6 Claims, 6 Drawing Sheets

(56) References Cited

U.S. PATENT DOCUMENTS

| | | | |
|---|---|---|---|
| 2014/0201126 A1* | 7/2014 | Zadeh | A61B 5/165 706/52 |
| 2019/0147588 A1* | 5/2019 | Rowley Grant | G06T 5/002 382/131 |
| 2020/0019823 A1* | 1/2020 | Wang | G06N 3/0454 |

* cited by examiner

DISCRIMINATION RESULT PROVIDING APPARATUS, OPERATING METHOD OF DISCRIMINATION RESULT PROVIDING APPARATUS, DISCRIMINATION RESULT PROVIDING PROGRAM, AND DISCRIMINATION RESULT PROVIDING SYSTEM

CROSS-REFERENCE TO RELATED APPLICATION

This application claims priority from Japanese Patent Application No. 2017-189992, filed on Sep. 29, 2017, the disclosure of which is incorporated by reference herein in its entirety.

BACKGROUND

Field of the Invention

The present invention relates to a discrimination result providing apparatus that provides a discrimination result of a discriminator generated through machine learning, an operating method of the discrimination result providing apparatus, a discrimination result providing program, and a discrimination result providing system.

Related Art

In the related art, machine learning has been used for performing recognition or classification of images or the like by learning features of data. In recent years, various learning methods have been developed, and a processing capacity of a computer has been improved to reduce a processing time, so that deep learning in which a system learns features of image data or the like at a deeper level has become possible. By performing deep learning, it is possible to recognize features of images or the like with very high accuracy, which leads to an expectation of improvements in discrimination performance.

In a medical field, artificial intelligence (AI) for recognizing features of images with high accuracy by performing learning using deep learning is desired. In the deep learning process, learning based on a large amount of high-quality data is necessary according to various purposes. To this end, it is important to efficiently prepare learning data. In each medical institution, image data on a large number of cases is accumulated with the spread of a picture archiving and communication system (PACS). Thus, learning using image data on various cases accumulated in each medical institution has been studied.

Further, in recent years, as AI has been used in various fields, AI provided in a computer on a cloud has been used through a network from various devices. Further, with diversification of various devices or upgrading of a communication technology, it is possible to provide various cloud services through a network. In such a distributed service, distribution of an optimal resource is performed so that an execution environment suitable for a change relating to an infrastructure or other factors can be provided. In a system disclosed in JP2011-154532A, a structure capable of evaluating provision of a service using a node of a participant and enabling usage of the service according to the evaluation result is disclosed. In this system, it is possible to allow usage of a service of a different person for the node of the participant as a consideration of provision of a service of the participant, and to request provision of the service of the participant as a condition of usage of a service of a different person. Further, it is possible for a user to obtain an authority for using a service, points, or the like according to evaluation of provision of the service.

In a medical field, expectations for utilization of AI are increasing, and medical support using AI is expected. However, in order to improve performance of AI, it is necessary to prepare a large amount of learning data for learning. It is necessary to assign correct solution data to the learning data, but an operation of assigning correct solution data is burdensome. Accordingly, if there is no direct merit for a user in creating learning data, it is difficult to provide a motivation for creating learning data, and consequently, it is difficult to collect a large amount of learning data.

SUMMARY

Accordingly, in order to solve the above-described problems, an object of the invention is to provide a discrimination result providing apparatus, an operating method of the discrimination result providing apparatus, a discrimination result providing program, and a discrimination result providing system that perform discrimination by performing learning with respect to a large amount of various learning data necessary for deep learning in a medical field.

According to an aspect of the invention, there is provided a discrimination result providing apparatus comprising: a reception section that receives, from a plurality of terminals that belong to a plurality of organizations, identification information for identifying the organizations and image correct solution data obtained by assigning correct solution data to an image through a network; a learning section that obtains a learning-terminated discriminator that is a discriminator that has performed learning using the received image correct solution data; and a discrimination result transmission section that transmits a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs.

According to another aspect of the invention, there is provided an operating method of a discrimination result providing apparatus including a reception section, a learning section, and a discrimination result transmission section, the method comprising: receiving, from a plurality of terminals that belong to a plurality of organizations, identification information for identifying the organizations and image correct solution data obtained by assigning correct solution data to an image through a network, using the reception section; obtaining a learning-terminated discriminator that is a discriminator that has performed learning using the received image correct solution data, using the learning section; and transmitting a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to identification information of an organization to which the terminal belongs, using the discrimination result transmission section.

According to a still another aspect of the invention, there is provided a discrimination result providing program that causes a computer to function as: a reception section that receives, from a plurality of terminals that belong to a plurality of organizations, identification information for identifying the organizations and image correct solution data obtained by assigning correct solution data to an image through a network; a learning section that obtains a learning-terminated discriminator that is a discriminator that has performed learning using the received image correct solution data; and a discrimination result transmission section that transmits a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs.

"A plurality of terminals that belong to a plurality of organizations" includes a case where one or more terminals belonging to one organization, but does not include a case where one terminal belongs to a plurality of organizations.

"The degree of performance improvement of a learning-terminated discriminator" may be a value or an index value considered to contribute to the performance improvement of the learning-terminated discriminator (in which the number of pieces of image correct solution data is excluded), and may not be a value obtained by evaluating whether the performance improvement is actually achieved. For example, there is a possibility that data to be used as image correct solution data may partially include data that is not correct solution data. Accordingly, it is possible to use a value obtained by manually or automatically measuring a correct solution rate of image correct solution data used for learning, instead of the number of pieces of image correct solution data used for learning.

"The resources" refer to hardware or an environment of hardware in which a program is capable of being used in a case where the program is executed using a central processing unit (CPU) in a computer.

Further, the resources may include a CPU utilization factor, a storage capacity, a memory capacity, a network band, or the number of accesses capable of being simultaneously performed from the terminals using the same identification information.

Further, the degree of performance improvement of the learning-terminated discriminator may be a correct solution rate of the image correct solution data received for each piece of identification information or a total sum of weights depending on loads in creating the image correct solution data received for each piece of identification information.

According to a still another aspect of the invention, there is provided a discrimination result providing system in which a discrimination result providing apparatus and a plurality of terminals that belong to a plurality of organizations are connected to each other through a network, in which the discrimination result providing apparatus comprises: a reception section that receives, from the plurality of terminals, identification information for identifying the organizations and image correct solution data obtained by assigning correct solution data to an image through a network; a learning section that obtains a learning-terminated discriminator that is a discriminator that has performed learning using the received image correct solution data; and a discrimination result transmission section that transmits a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs, and the terminal comprises: an image correct solution data transmission section that transmits the identification information and the image correct solution data to the discrimination result providing apparatus through the network; and a discrimination result acquisition section that transmits the discrimination target image to the discrimination result providing apparatus and receives the discrimination result from the discrimination result providing apparatus through the network.

According to a still another aspect of the invention, there is provided a discrimination result providing apparatus includes a memory that stores a command for causing a computer to execute and a processor configured to execute the stored command, in which the processor executes a process of receiving, from a plurality of terminals that belong to a plurality of organizations, identification information for identifying the organizations and image correct solution data obtained by assigning correct solution data to an image through a network; a process of obtaining a learning-terminated discriminator that is a discriminator that has performed learning using the received image correct solution data; and a process of transmitting a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs, using the discrimination result transmission section.

According to the invention, image correct solution data is received from a plurality of terminals that belong to a plurality of organizations, a learning-terminated discriminator that is a discriminator that has performed learning using the image correct solution data is obtained, and a discrimination result obtained by determining distribution of resources capable of being used by the discriminator in accordance with the number of pieces of the received image correct solution data or the degree of performance improvement of the learning-terminated discriminator using the image correct solution data is transmitted to a terminal and performing discrimination with respect to a discrimination target image received from a corresponding terminal using the resources of the determined distribution, is transmitted to the terminal that is a transmission source. Thus, it is possible to improve discrimination performance of a discriminator using a large amount of image correct solution data from multiple organizations. Further, in accordance with the degree of contribution to image correct solution data provided from each terminal, discrimination is performed by a learning-terminated discriminator using distributed resources, and thus, it is possible to provide a motivation for creating image correct solution data, and consequently, it is possible to collect a large amount of image correct solution data.

DETAILED DESCRIPTION

Figure 1:
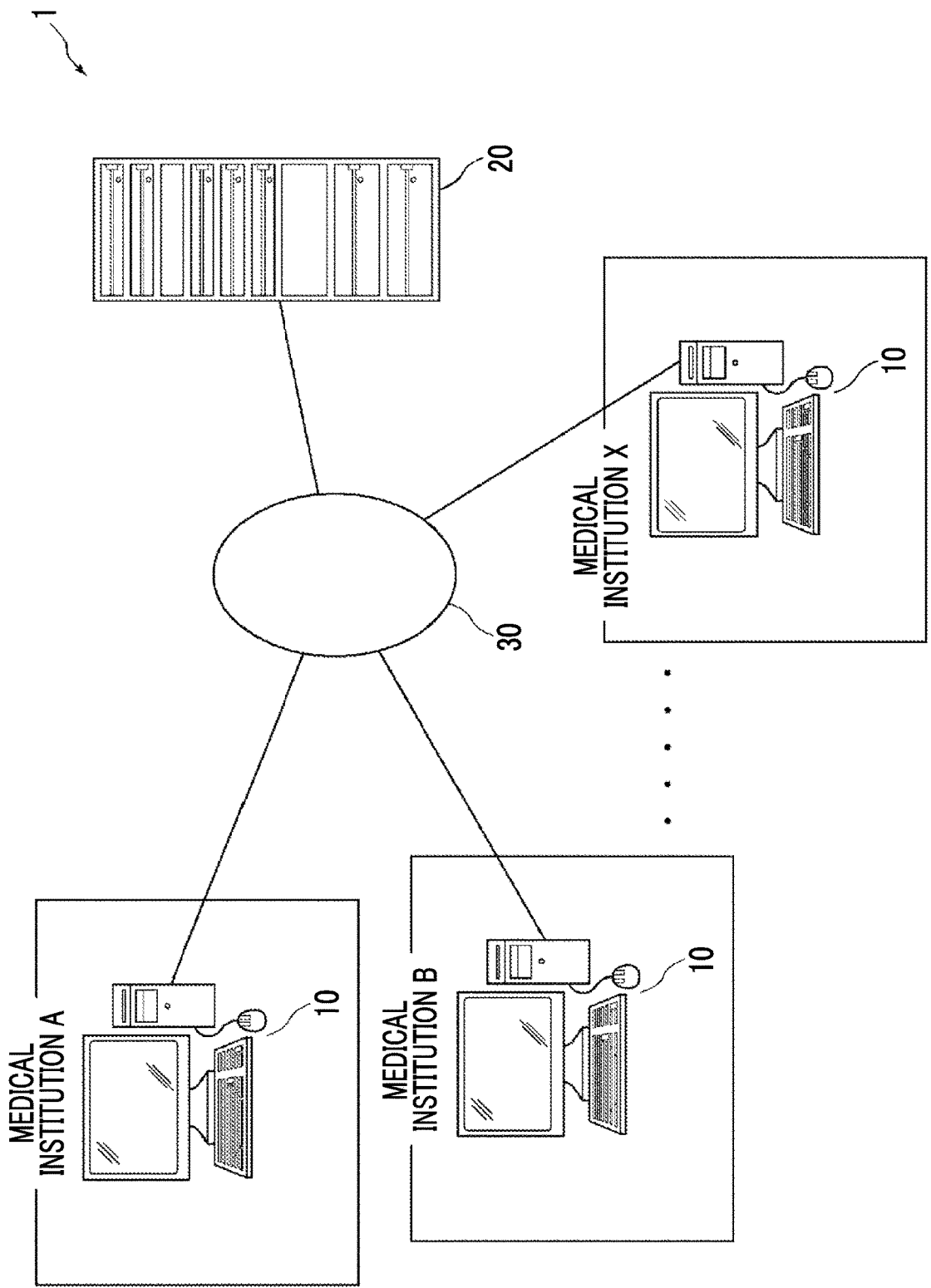
FIG. 1 is a diagram showing a schematic configuration of a discrimination result providing system according to the invention.

An embodiment of the invention will be described with reference to the accompanying drawings. In this embodiment, a case where an organization is a medical institution will be described as an example. FIG. 1 shows a schematic configuration of a discrimination result providing system 1 according to an embodiment of the invention. The discrimination result providing system 1 has a configuration in which a plurality of terminals 10 provided in a plurality of medical institutions A, B, . . . , and X and a discrimination result providing apparatus 20 disposed on a cloud side are connected to each other through a network 30. The plurality of terminals 10 may be provided in each medical institution.

The discrimination result providing apparatus 20 is a high-performance computer having a server function, which includes a known hardware configuration such as a CPU, a memory, a storage, an input/output interface, a communication interface, a data bus, and the like. Further, in the discrimination result providing apparatus 20, a known operation system or the like is installed. Further, a graphics processing unit (GUP) may be provided as necessary. Alternatively, the discrimination result providing apparatus 20 may be provided using a plurality of computers. As a discrimination result providing program according to the invention is installed in a computer and a command of the program is executed by a CPU of the computer, the discrimination result providing apparatus 20 functions as a discrimination result providing apparatus.

The terminals 10 are computers provided in the respective medical institutions A, B, . . . , and X, and each terminal 10 has a known hardware configuration such as a CPU, a memory, a storage, an input/output interface, a communication interface, an input device, a display device, a data bus, and the like. The terminal 10 includes a display as the display device. Further, in the terminals 10, a known operation system or the like is installed. Further, a GUP may be provided as necessary.

The network 30 is a wide area network (WAN) that connects the terminals 10 disposed in the plurality of medical institutions A, B, . . . , and X and the discrimination result providing apparatus 20 in a wide area through a public line network or a leased line network.

Figure 2:
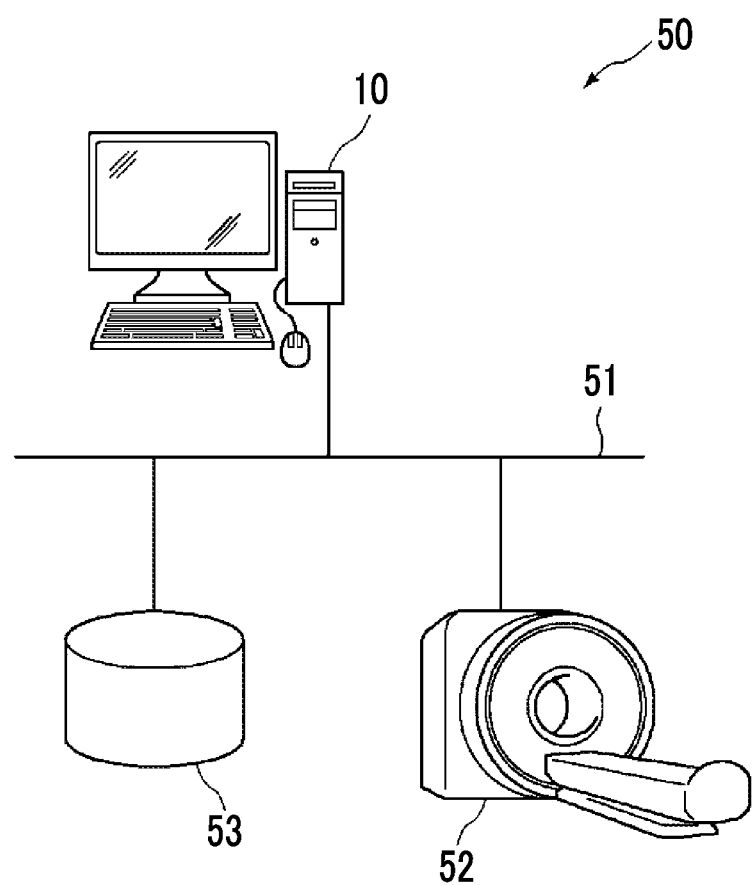
FIG. 2 is a diagram showing a schematic configuration of a medical information system.

Further, the terminal 10 is connected to a medical information system 50 of each of the medical institutions A, B, . . . , and X through a local area network (LAN) 51, as shown in FIG. 2. The medical information system 50 includes a modality (imaging device) 52 and an image database 53, and is configured to perform transmission and reception of image data with respect to other medical information systems 50 through the network 51. It is preferable that the network 51 uses a communication cable such as an optical fiber so as to transfer image data at high speed.

The modality 52 includes a device that images an inspection target portion of a subject to generate an inspection image that represents the inspection target portion and adds accessory information regulated in the DICOM standard to the inspection image for output. As a specific example, a computed tomography (CT) apparatus, a magnetic resonance imaging (MRI) apparatus, a PET (positron emission tomography) apparatus, an ultrasound apparatus, a computed radiography (CR) apparatus that uses a flat panel detector (FPD), or the like may be used.

In the image database 53, a software program that provides a function of a data base management system (DBMS) to a general-purpose computer is inserted, and the image database 53 includes a large capacity storage. The storage may be a large capacity hard disk drive, or may be a network attached storage (NAS) connected to the network 51 or a disk drive connected to a storage area network (SAN). Further, image data obtained through imaging in the modality 52 is transmitted to the image database 53 through the network 51 for storage according to a storage format and a communication standard based on the DICOM standard.

In this embodiment, an example in which an image processing program in which a discriminator that functions as an actually operating discriminator is inserted and a learning program in which a discriminator that functions as a learning discriminator is inserted are installed in the discrimination result providing apparatus 20 will be described.

Further, a case where the actually operating discriminator and the learning discriminator are a multi-layered neural network in which deep learning is performed to discriminate any one of plural types of organ regions and/or lesion regions will be described. In the multi-layered neural network, with respect to a plurality of pieces of different computational result data obtained in a pre-stage layer with respect to input data, that is, feature amount extraction result data, computational processing is performed using various kernels in respective layers. Then, feature amount data obtained in this way is acquired, and computational processing is further performed in next-stage and subsequent processing layers with respect to the feature amount data. Thus, it is possible to improve a recognition rate of a feature amount, and to discriminate which one of plural types of regions the input image data corresponds to.

Figure 3:
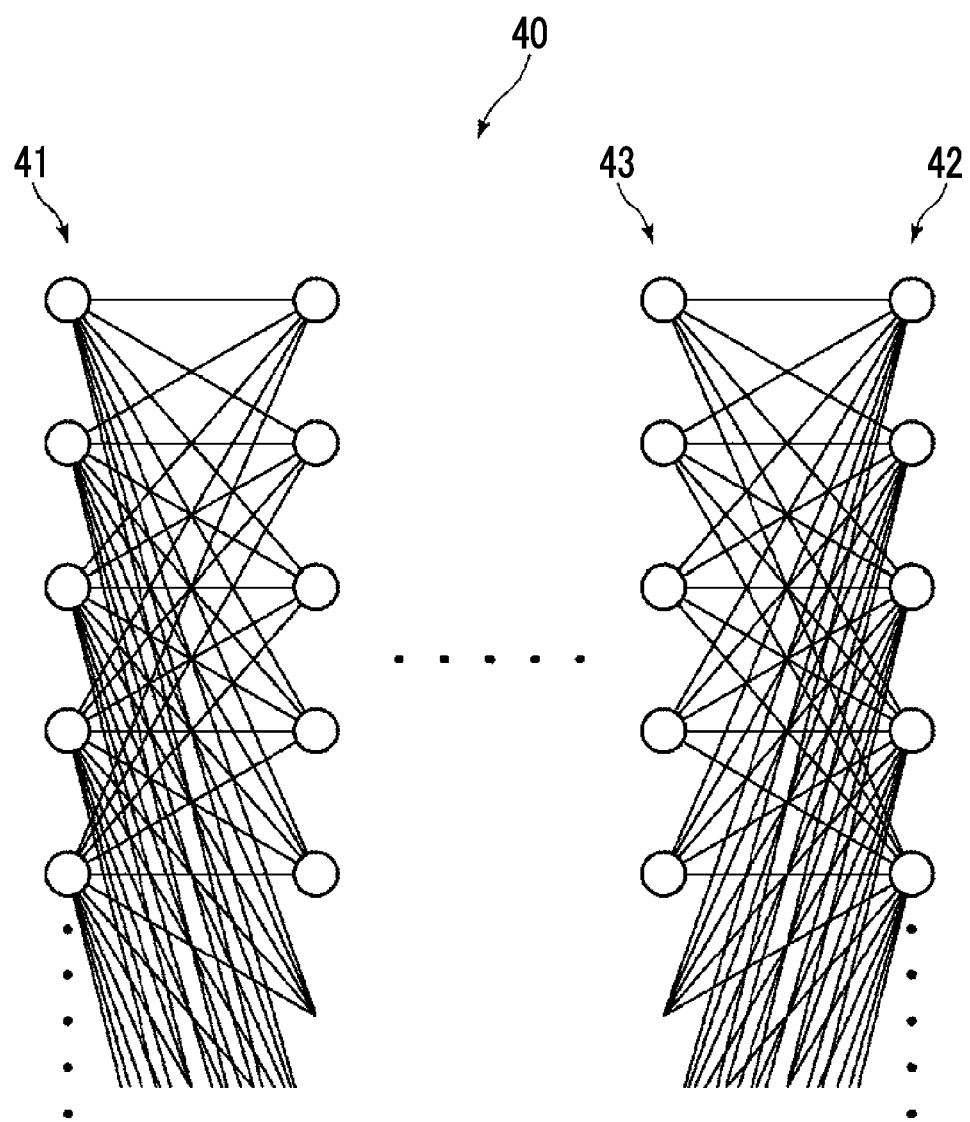
FIG. 3 is a diagram showing an example of a multi-layered neural network.

FIG. 3 is a diagram showing an example of a multi-layered neural network. As shown in FIG. 3, a multi-layered neural network 40 is formed of a plurality of layers including an input layer 41 and an output layer 42. In FIG. 3, a reference numeral 43 is given to a layer in front of the output layer 42.

The multi-layered neural network 40 is configured so that image data is input to the input layer 41 and a discrimination result of a region is output. When performing learning, the output discrimination result is compared with correct solution data, and coupling weights, between respective layers, of units (indicated by circles in FIG. 3) included in each layer of the multi-layered neural network 40 are modified from an output side (the output layer 42) toward an input side (input layer 41). Further, the modification of the coupling weights is repeatedly performed a predetermined number of times, or until a correct solution rate of the output discrimination result reaches 100% or becomes equal to or greater than a predetermined threshold value, using image data with multiple pieces of correct solution data, and then, the learning is terminated.

Further, in the discrimination result providing apparatus 20, a plurality of virtual servers capable of being connected from the terminal 10 of each medical institution are provided for the respective medical institutions, and allocation of resources such as a CPU utilization factor, a storage capacity, a memory capacity, a network band, or the number of accesses capable of being simultaneously performed from the terminals 10 using the same identification information is set. Hereinafter, a case where a virtual server is provided for each medical institution and allocation of resources is performed for each virtual server of each medical institution will be described. Further, identification information for identifying a medical institution is uniquely allocated.

Figure 4:
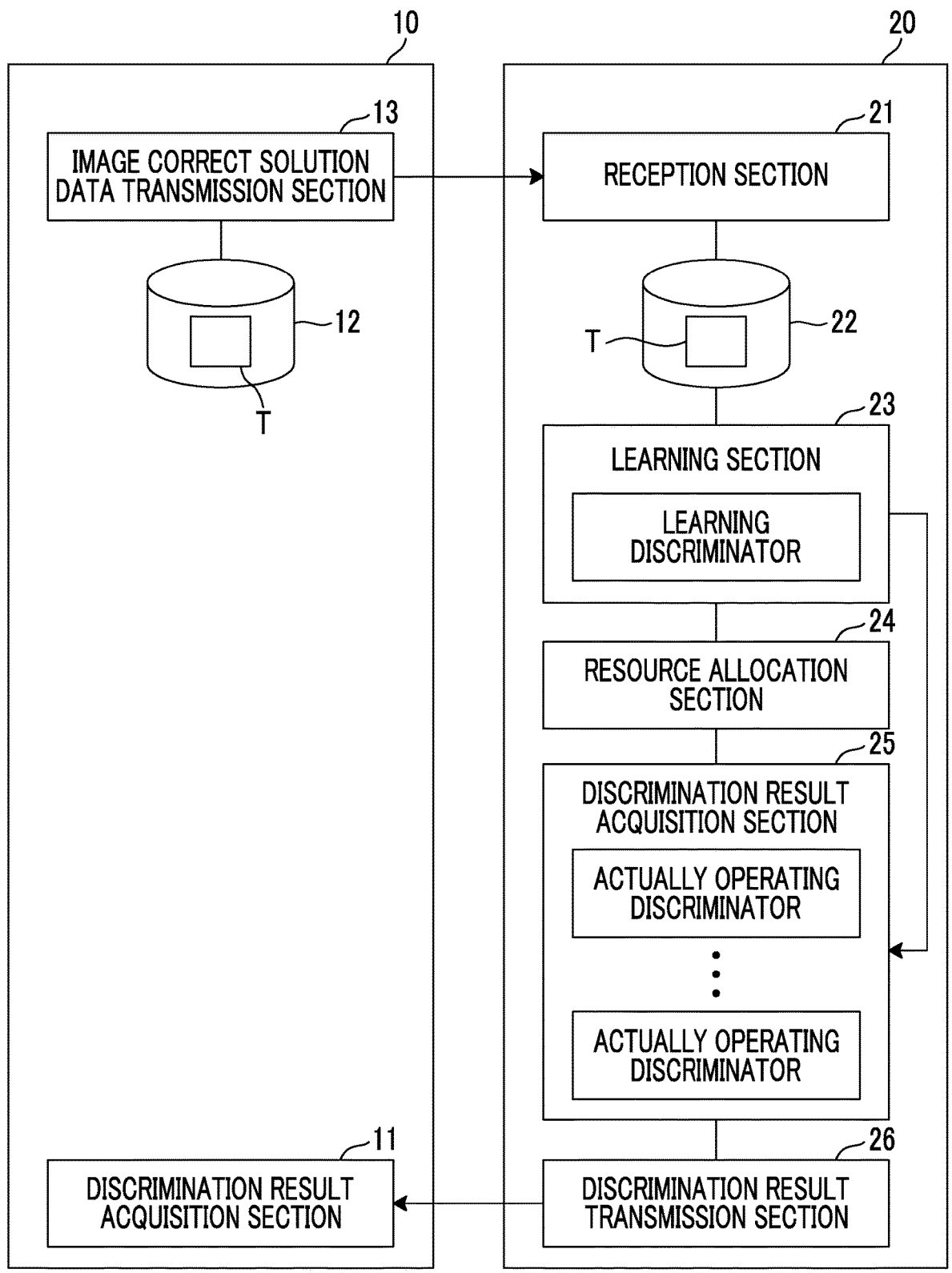
FIG. 4 is a block diagram showing a schematic configuration of a terminal and a discrimination result providing apparatus.

FIG. 4 is a block diagram showing a schematic configuration of the terminal 10 and the discrimination result providing apparatus 20. Functions of the terminal 10 and the discrimination result providing apparatus 20 will be described in detail with reference to FIG. 4.

First, the discrimination result providing apparatus 20 will be described. As shown in FIG. 4, the discrimination result providing apparatus 20 includes a reception section 21, an image correct solution data storage section 22, a learning section 23, a resource allocation section 24, a discrimination result acquisition section 25, and a discrimination result transmission section 26.

The discrimination result acquisition section 25 achieves a discrimination result using a configuration in which an actually operating discriminator (a learning-terminated discriminator) functions by executing an image processing program on a virtual server relating to each medical institution, the actually operating discriminator is provided in the discrimination result providing apparatus 20 for each medical institution, and a discrimination target image received from the terminal 10 of each medical institution through a network is input to the actually operating discriminator. The image processing program is executed using resources that are set on each virtual server.

The discrimination result transmission section 26 transmits a discrimination result obtained in the discrimination result acquisition section 25 to the terminal 10 that is a transmission source of the discrimination target image through the network.

The reception section 21 receives an identification information ID of each medical institution and image correct solution data T from each terminal 10. The received image correct solution data T is registered in the image correct solution data storage section 22 in association with the identification information ID of the medical institution that is a transmission source. The image correct solution data T is formed of image data and correct solution data of the image data. The correct solution data includes both of a mask image indicating a region such as an organ or an abnormal shade in image data and information indicating what the region of the mask image is (for example, whether the region is a region of an organ such as the liver, the kidneys or lung fields, or a region of an abnormal shade such as a liver cancer, a kidney cancer or a pulmonary nodule).

The learning section 23 causes the multi-layered neural network 40 of a learning discriminator provided in a learning program to perform learning using the image correct solution data T stored in the image correct solution data storage section 22. The learning discriminator performs learning with respect to the image correct solution data T received from all the medical institutions registered in the image correct solution data storage section 22.

Further, the learning section 23 considers the learning discriminator as a learning-terminated discriminator, in a stage where the learning of the learning discriminator progresses to some extent, and generates an image processing program of a new version in which the learning-terminated discriminator is inserted. Specifically, the learning of the image correct solution data is repeatedly performed a predetermined number of times or for a predetermined period of time to generate an image processing program of a new version. Periodically, an image processing program on a virtual server for each medical institution is replaced with an image processing program of a new version. Thus, an actually operating discriminator is updated to a new learning-terminated discriminator to function as a new actually operating discriminator. With respect to software for the purpose of health care, since the software should be pursuant to the Pharmaceuticals Medical Equipment Law (revised Pharmaceutical Affairs Law), a criterion determined by the Pharmaceuticals Medical Equipment Law needs to be cleared. Thus, it is preferable to prepare in advance an image set for evaluation formed by a combination of a plurality of images capable of being evaluated according to the criterion determined by the Pharmaceuticals Medical Equipment Law, and to use a learning-terminated discriminator in which a correct solution rate of the image set for evaluation exceeds a predetermined reference value as an actually operating discriminator.

The resource allocation section 24 calculates the number of pieces of image correct solution data T learned by the learning section 23 or the degree of performance improvement of the learning-terminated discriminator for each identification information ID, and determines distribution of resources capable of being used by a virtual server for each identification information ID, that is, distribution of resources capable of being used by an actually operating discriminator (learning-terminated discriminator).

(a) For example, the image correct solution data T stored in the image correct solution data storage section 22 is counted for each piece of identification information to calculate the number of pieces of image correct solution data T registered in each medical institution for each medical institution. According to the calculated number, the distribution of the resources is determined. For example, when the number of pieces of image correct solution data T registered in all the medical institutions is 1000, in a case where the number of pieces of image correct solution data T registered in the medical institution A is 100, distribution of resources to a virtual server with respect to the medical institution A occupies 10 (=100/1000)%.

(b) Further, as the degree of performance improvement, the correct solution rate of the image correct solution data T registered in each medical institution may be calculated, so that the resources may be allocated. For example, using the learning-terminated discriminator that has performed learning with respect to the image correct solution data T registered in all the medical institutions, the accuracy of the image correct solution data T registered from each medical institution is determined. In a case where a discrimination result obtained by inputting image data of image correct solution data T of a certain medical institution to the learning-terminated discriminator and correct solution data of the image correct solution data T match each other, it is automatically determined that the image correct solution data T is a correct solution. In this way, by determining whether the image correct solution data T registered in each medical institution is a correct solution, the correct solution rate of the image correct solution data T registered in each medical institution is calculated. In a case where a correct solution rate obtained by evaluating image correct solution data T of the medical institution A using a learning-terminated discriminator is 50%, a correct solution rate in the medical institution B is 70%, and a correct solution rate in the medical institution C is 30%, the distribution of the resources to the virtual server of the medical institution A occupies 33% (=50/(50+70+30)).

Alternatively, for example, a doctor may observe an image to determine whether the image correct solution data T is a correct solution, and may manually record a correct solution mark in the image correct solution data T to calculate a correct solution rate. The correct solution rate may be calculated by a combination of the automatic determination of whether the image correct solution data T is a correct solution using a learning-terminated discriminator and the manual determination of a doctor or the like.

(c) Further, as the degree of performance improvement, a total sum of weights depending on loads in creating the image correct solution data T registered in each medical institution may be calculated to allocate resources. Weighting is performed with respect to creation loads of learning data, a total sum of values obtained by multiplying a weight coefficient by the number of pieces of learning data registered in each medical institution is calculated, and distribution of resources is determined in accordance with the total sum in each medical institution. For example, (1) only check marking is performed, (2) correct labeling is performed with respect to a mask image indicating a region on an image, and (3) a mask image in which a correct region is painted on an image is generated. In this case, the degree of difficulty becomes higher from (1) to (3), in which a coefficient of (1) is set to 1.0, a coefficient of (2) is set to 1.5, and a coefficient of (3) is set to 2.0. In the medical institution A, in a case where the number of cases (1) is 50, the number of cases (2) is 20, and the number of cases (3) is 10, a total sum of weights in the medical institution A becomes 1.0*50+1.5*20+2.0*10=100. Similarly, a total sum of weights in a different medical institution is calculated. In a case where the total sum in all the medical institutions is 1000, the distribution of the resources to the virtual server with respect to the medical institution A occupies 10 (=100/1000)%.

(d) Further, as the degree of performance improvement, weighting may be performed in accordance with a rarity of learning data (for example, whether a region corresponds to a rare lesion or the like), the number of pieces of learning data registered in each medical institution may be multiplied by a weight to calculate a total sum of weights in each medical institution, and distribution of resources may be determined in accordance with the total sum in each medical institution. The total sum of the weights is calculated in a similar way to the case of (c), so that the distribution of the resources is performed.

(e) Alternatively, the degree of performance improvement of a learning discriminator of the learned image correct solution data T may be calculated to allocate resources. In a case where a difference between correct solution rates of initial to current learning discriminators is 100, the degree of performance improvement is determined on the basis of an increase rate of a correct solution rate of a learning discriminator due to learning of registered image correct solution data T. The correct solution rate may be calculated using an image set for evaluation. For example, when the initial correct solution rate is 70% and the current correct solution rate of the learning discriminators that have performed learning with respect to the image correct solution data T of all the medical institutions to be learned is 85%, in a case where a correct solution rate of a learning-terminated discriminator that has performed learning using the image correct solution data T registered in the medical institution A is increased by 5%, the distribution of the resources occupies 33 (≈5/15)%.

In the above description, a method for calculating distribution of resources as ratios at which all the resources are allocated to respective medical institutions has been described as an example, but CPU utilization factors, storage capacities, memory capacities, network bands, the number of accesses capable of being simultaneously performed from terminals using the same identification information, or the like may be distributed at different ratios. Further, in accordance with load situations of respective virtual machines, distribution of resources may be changed. In accordance with ratios of distribution of resources obtained by the resource allocation section 24, the resources may be distributed so that a processing performance of a program operated on a virtual server becomes higher in a medical institution with a higher ratio.

The distribution of the resources is updated whenever correct solution image data is registered from each terminal 10. Alternatively, an increase rate of a correct solution rate of a learning discriminator may be calculated at a predetermined timing to update the distribution of the resources depending on performance improvement.

The discrimination result acquisition section 25 executes an image processing program on a virtual server based on distribution of resources that are frequently updated in accordance with the number of pieces of image correct solution data received for each identification information ID or the degree of performance improvement of a learning-terminated discriminator through learning using the image correct solution data received for each identification information ID, to thereby acquire a discrimination result of an actually operating discriminator.

Next, the terminal 10 will be described. As shown in FIG. 4, the terminal 10 includes a discrimination result acquisition section 11, an image correct solution data storage section 12, and an image correct solution data transmission section 13.

The discrimination result acquisition section 11 transmits a discrimination target image to the discrimination result providing apparatus 20 through a network 30, and receives an obtained discrimination result of the discrimination target image through the network 30. In a case where each terminal 10 is connected to the discrimination result providing apparatus 20, the terminal 10 is connected to a virtual server provided in each medical institution, and is able to use an actually operating discriminator that is executed on each virtual server. The terminal 10 inputs the discrimination target image to the actually operating discriminator on the virtual server, and receives an output discrimination result through the network 30.

The image correct solution data storage section 12 stores image correct solution data T. The correct solution data is created by observation of image data from a user such as a radiologist of each of medical institutions A, B, . . . , and X. For example, image data is extracted from an image database 53, and is input to the discrimination result acquisition section 11 to acquire a discrimination result. Then, it is determined whether the discrimination result is a correct solution or an incorrect solution by a radiologist. In a case where the discrimination result is the correct solution, using the discrimination result as correct solution data, both of the input image data and the correct solution data are stored in the image correct solution data storage section 12 as image correct solution data T. In a case where the discrimination result is the incorrect solution, the user generates a mask image of correct solution data. Then, the correct solution data is assigned to the image data, and the result is stored in the image correct solution data storage section 12 as image correct solution data T.

The image correct solution data transmission section 13 transmits the image correct solution data T stored in the image correct solution data storage section 12 to the discrimination result providing apparatus 20 through the network 30.

Next, a processing flow of a deep learning process according to this embodiment of the invention will be described with reference to a transition chart of FIG. 5 and a flowchart of FIG. 6.

First, the discrimination result providing apparatus 20 is caused to execute an actually operating discriminator NNo and a learning discriminator NNt, respectively (S1 and S2). Further, the actually operating discriminator NNo is executed on a virtual server of each medical institution.

Each terminal 10 generates correct solution data with respect to image data, and stores image correct solution data T in which the image data and the correct solution data are associated with each other in a storage (image correct solution data storage section 12) (S3). A user logs into the discrimination result providing apparatus 20 from each terminal 10 is performed, so that identification information ID of each medical institution is transmitted to the discrimination result providing apparatus 20 (S4). Further, the image correct solution data transmission section 13 transmits the image correct solution data T stored in the storage to the discrimination result providing apparatus 20 (S5).

The discrimination result providing apparatus 20 receives the image correct solution data T from each terminal 10 through the reception section 21 (S6). The received image correct solution data T is registered in the image correct solution data storage section 22 in association with the identification information ID of the medical institution that is a transmission source. The learning section 23 causes the learning discriminator NNt to perform learning using the image correct solution data T stored in the image correct solution data storage section 22 (S7) (see broken lines of (1) in FIG. 5).

Further, the resource allocation section 24 calculates the number of pieces of the learned image correct solution data T or the degree of performance improvement of a learning-terminated discriminator for each identification information ID, and determines distribution of resources capable of being used in the virtual server (see FIG. 5, frames A, B, . . . , and X of solid lines) for each identification information ID (S8). The discrimination result acquisition section 25 updates the distribution of the resources of the actually operating discriminators NNo executed on the virtual servers A, B, . . . , and X in accordance with the distribution determined by the resource allocation section 24 (S9). Until the learning of the image correct solution data T is performed a predetermined number of times, or for a predetermined period of time, the processes of S6 to S9 are repeated (S10).

Figure 5:
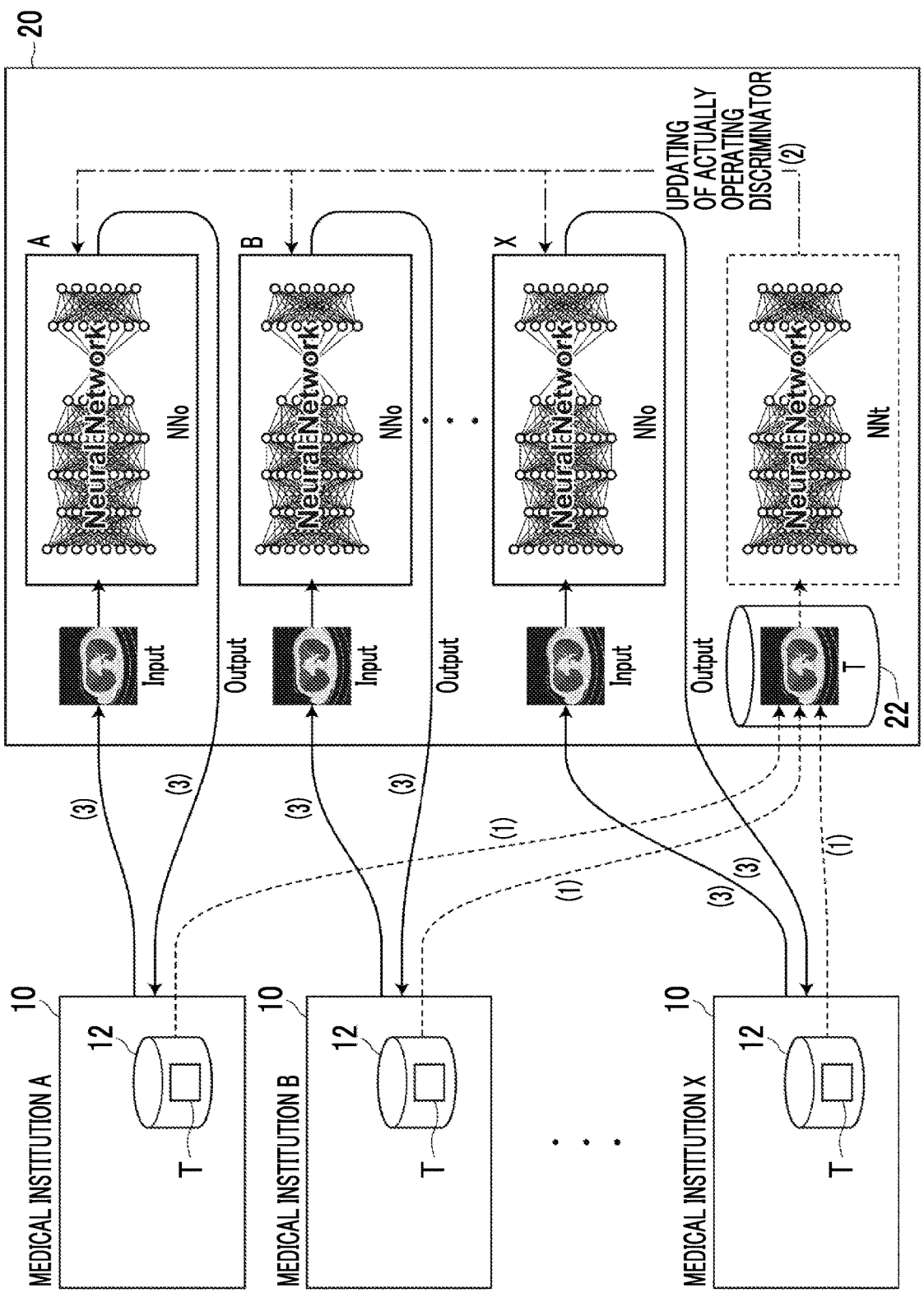
FIG. 5 is a diagram for illustrating a learning method of a discriminator and a method for acquiring a discrimination result using an actually operating discriminator.
Figure 6:
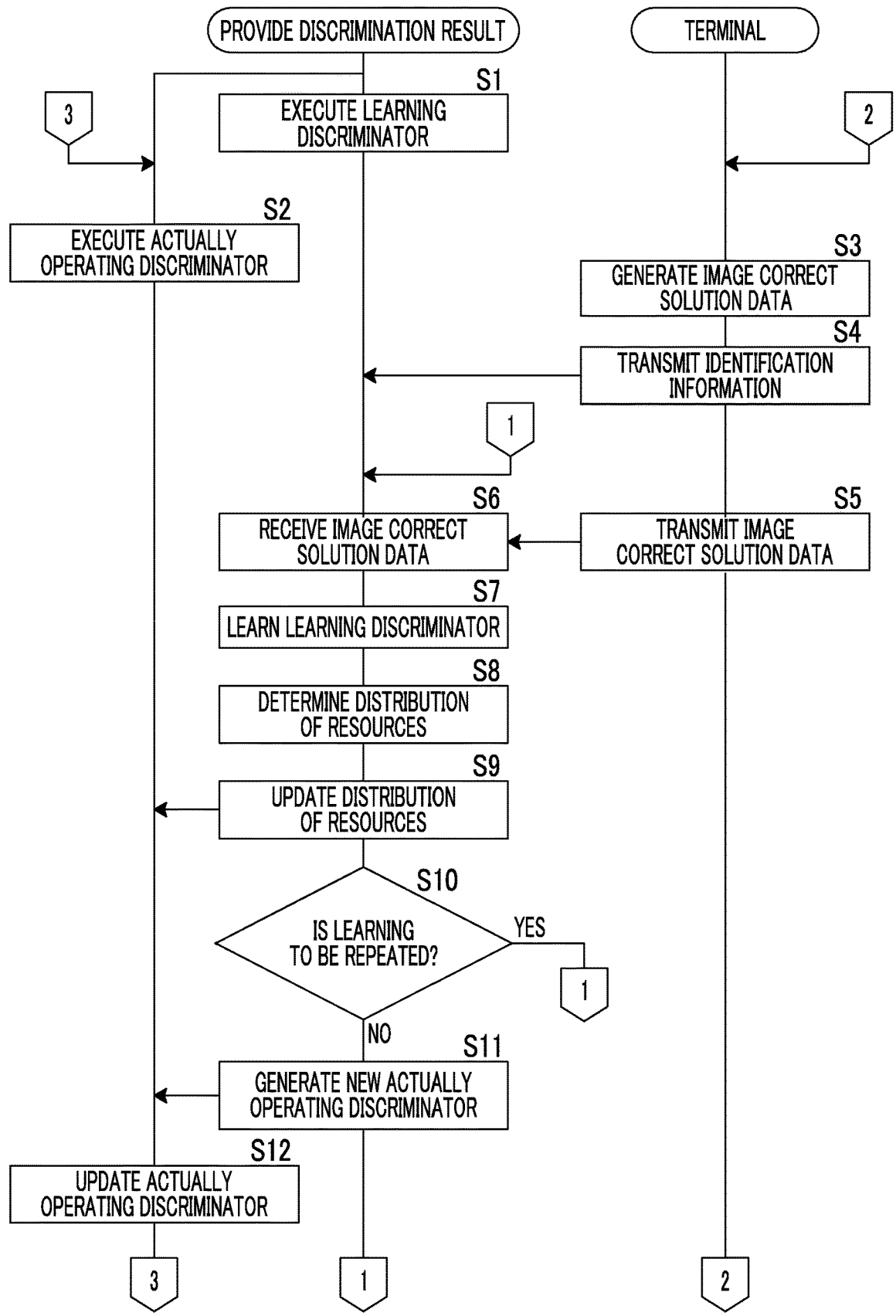
FIG. 6 is a flowchart showing a flow of a process to be learned by a discriminator.

Further, the learning section 23 considers a learning-terminated discriminator that has performed learning with respect to the image correct solution data T, which is the learning discriminator NNt, as a new actually operating discriminator NNo (S11), and updates the actually operating discriminator NNo on the virtual server of each medical institution (S12) (see a single-dot chain line (2) in FIG. 5).

As described above, by repeating the processes of S2 to S12, it is possible to learn the image correct solution data T provided from various medical institutions, to thereby improve performance of discriminators.

On the other hand, the user logs into the discrimination result providing apparatus 20 from the terminal 10, so that the terminal 10 is connected to each of the virtual servers A, B, . . . , and X for the respective medical institutions. Further, the discrimination result acquisition section 11 transmits a discrimination target image "Input" to the discrimination result providing apparatus 20, and acquires a discrimination result "Output" (see solid lines (3) in FIG. 5). The terminal 10 is able to use a periodically updated actually operating discriminator NNo. Further, in accordance with distribution of resources depending on the number of pieces of image correct solution data T registered in each medical institution or the degree of contribution to improvement of performance of a learning-terminated discriminator, it is possible to use the actually operating discriminator NNo from the terminal 10.

Hereinbefore, as described above, in this embodiment of the invention, as the number of image correct solution data generated and registered by a user becomes larger, or as the degree of contribution to improvement of performance of a discriminator due to the image correct solution data registered by the user becomes higher, by increasing distribution of resources to a learning-terminated discriminator of the user, that is, an actually operating discriminator, it is possible to perform discrimination of an image in a comfortable execution environment. In this way, due to a configuration in which a user can directly receive benefits, it is possible to provide a motivation for creating image correct solution data, and consequently, it is possible to collect a large amount of image correct solution data.

In the above description, an example where distribution of resources is determined for each medical institution is shown, but a configuration in which allocation of identification information and management of registration of image correct solution data are performed in the unit of terminals or in the unit of users such as a radiologist and distribution of resources is determined in the unit of terminals or in the unit of users may be used. With such a configuration, it is possible to provide more motivation to individuals, and thus, it is possible to collect a large amount of image correct solution data.

In this embodiment, an example in which distribution of resources is performed with respect to virtual servers is shown, but a configuration in which there is provided a hypervisor in which virtual servers are disposed between hardware and an OS and physical resources are divided into a plurality of virtual machines may be used, or a configuration in which virtualization software is installed on an OS of a physical server and a plurality of virtualization environments are operated thereon may be used.

In the above description, an example where a discrimination result providing apparatus and a terminal functions on a general-purpose computer is shown, but a configuration in which an exclusive circuit such as an application specific integrated circuit (ASIC) or a field programmable gate arrays (FPGA) that permanently stores a program for executing a part of the functions is provided may be used. Alternatively, a configuration in which a program command stored in an exclusive circuit and a program command executed by a genera-purpose CPU that is programmed to use the program in the exclusive circuit are combined may be used. As described above, program commands may be executed by any combination of hardware configurations of a computer.

What is claimed is:

1. A discrimination result providing apparatus comprising:
    a processor configured to:
        receive, from a plurality of terminals that belong to a plurality of organizations, identification information for identifying the organizations and image correct solution data obtained by assigning correct solution data to an image through a network;
        obtain a learning-terminated discriminator that is a discriminator that has performed learning using the received image correct solution data; and
        transmit a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs.

2. The discrimination result providing apparatus according to claim 1,
    wherein the resources include a CPU utilization factor, a storage capacity, a memory capacity, a network band, or the number of accesses capable of being simultaneously performed from the terminals using the same identification information.

3. The discrimination result providing apparatus according to claim 1,
    wherein the degree of performance improvement of the learning-terminated discriminator is a correct solution rate of the image correct solution data received for the each piece of identification information or a total sum of weights depending on loads in creating the image correct solution data received for the each piece of identification information.

4. An operating method of a discrimination result providing apparatus, the method comprising:
    receiving, from a plurality of terminals that belong to a plurality of organizations, identification information for identifying the organizations and image correct solution data obtained by assigning correct solution data to an image through a network;
    obtaining a learning-terminated discriminator that is a discriminator that has performed learning using the received image correct solution data; and
    transmitting a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs.

5. A non-transitory computer-readable recording medium storing therein a discrimination result providing program that causes a computer to:
    receive, from a plurality of terminals that belong to a plurality of organizations, identification information for identifying the organizations and image correct solution data obtained by assigning correct solution data to an image through a network;
    obtain a learning-terminated discriminator that is a discriminator that has performed learning using the received image correct solution data; and
    transmit a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs.

6. A discrimination result providing system in which a discrimination result providing apparatus and a plurality of terminals that belong to a plurality of organizations are connected to each other through a network,
wherein the discrimination result providing apparatus comprises a processor configured to:
receive, from the plurality of terminals, identification information for identifying the organizations and image correct solution data obtained by assigning correct solution data to an image through a network;
obtain a learning-terminated discriminator that is a discriminator that has performed learning using the received image correct solution data; and
transmit a discrimination result to the terminal that is a transmission source of a discrimination target image through the network, the discrimination result being obtained by determining distribution of resources capable of being used by the learning-terminated discriminator in accordance with the number of pieces of the image correct solution data received for each piece of identification information or the degree of performance improvement of the learning-terminated discriminator through learning using the image correct solution data received for the each piece of identification information and performing, by the learning-terminated discriminator, discrimination with respect to the discrimination target image received from the terminal using the resources of the determined distribution with respect to the identification information of the organization to which the terminal belongs, and
wherein the terminal comprises a terminal processor configured to:
transmit the identification information and the image correct solution data to the discrimination result providing apparatus through the network; and
transmit the discrimination target image to the discrimination result providing apparatus and receive the discrimination result from the discrimination result providing apparatus through the network.

* * * * *